United States Patent
Nakajima et al.

(10) Patent No.: US 11,667,937 B2
(45) Date of Patent: Jun. 6, 2023

(54) METHOD FOR PRODUCING UROLITHINS

(71) Applicant: DAICEL CORPORATION, Osaka (JP)

(72) Inventors: Takanori Nakajima, Tokyo (JP); Hiroaki Yamamoto, Tokyo (JP)

(73) Assignee: DAICEL CORPORATION, Osaka (JP)

(*) Notice: Subject to any disclaimer, the term of this patent is extended or adjusted under 35 U.S.C. 154(b) by 0 days.

(21) Appl. No.: 16/957,663

(22) PCT Filed: Sep. 20, 2018

(86) PCT No.: PCT/JP2018/034916
§ 371 (c)(1),
(2) Date: Jun. 24, 2020

(87) PCT Pub. No.: WO2019/130681
PCT Pub. Date: Jul. 4, 2019

(65) Prior Publication Data
US 2020/0332323 A1  Oct. 22, 2020

(30) Foreign Application Priority Data
Dec. 26, 2017  (WO) .................. PCT/JP2017/046789

(51) Int. Cl.
*C12P 17/06* (2006.01)
*C12N 1/20* (2006.01)
*C12R 1/01* (2006.01)

(52) U.S. Cl.
CPC .............. *C12P 17/06* (2013.01); *C12N 1/205* (2021.05); *C12R 2001/01* (2021.05)

(58) Field of Classification Search
None
See application file for complete search history.

(56) References Cited

U.S. PATENT DOCUMENTS

| | | | | |
|---|---|---|---|---|
| 11,066,381 | B2 * | 7/2021 | Nakajima | A61P 29/00 |
| 11,168,300 | B2 * | 11/2021 | Kudoh | C12P 17/06 |
| 2019/0323045 | A1 * | 10/2019 | Kudoh | C12N 1/205 |
| 2020/0332323 | A1 * | 10/2020 | Nakajima | C12P 17/06 |

FOREIGN PATENT DOCUMENTS

| | | | |
|---|---|---|---|
| EP | 3561067 A1 | 10/2019 | |
| WO | WO 2014/147280 A1 | 9/2014 | |

OTHER PUBLICATIONS

Beltran et al., "Ellagibacter isourolithinifaciens gen. nov. sp. nov., a new member of the family Eggerthellaceae, isolated from human gut", International Journal of Systematic and Evolutionary Microbiology, vol. 68, No. 5, 2018, pp. 1707-1712.
Selma et al., "Isolation of Human Intestinal Bacteria Capable of Producing the Bioactive Metabolite Isourolithin A from Ellagic Acid", Frontiers in Microbiology, vol. 8, 2017, Article 1521.
EESR issued in the corresponding EP patent application No. 18897539.5, dated Mar. 5, 2021.
Giménez-Bastida et al., J. Agric. Food Chem., vol. 60, 2012, pp. 8866-8876.
Ishimoto et al., Biosci. Biotechnol. Biochem., vol. 76, No. 2, 2012, pp. 395-399.
Ito et al., J. Agric. Food Chem., vol. 56, 2008, pp. 393-400.
Nuñez-Sánchez et al., Mol. Nutr. Food Res., vol. 58, 2014, pp. 1199-1211.
Ryu et al., Nature Medicine, vol. 22, 2016, pp. 879-888.
Selma et al., Food Func., vol. 5, No. 8, 2014, pp. 1779-1784.
Verzelloni et al., Mol. Nutr. Food Res., vol. 55, 2011, S35-S43.
International search report issued in application No. PCT/JP2018/034916, dated Dec. 25, 2018.

* cited by examiner

*Primary Examiner* — Hope A Robinson
(74) *Attorney, Agent, or Firm* — Knobbe, Martens, Olson & Bear LLP

(57) ABSTRACT

An object of the present invention is to provide a method for eliminating the hydroxyl group at the 8-position of a urolithin to produce another kind of urolithin, and this object is achieved by a method for producing a second urolithin, comprising allowing, in a solution containing a first urolithin, a microorganism having an ability to produce the second urolithin from the first urolithin.

13 Claims, No Drawings

METHOD FOR PRODUCING UROLITHINS

CROSS REFERENCE TO RELATED APPLICATIONS

This application is a U.S. National Phase of International Application No. PCT/JP2018/034916, filed on Sep. 20, 2018, which claimed priority to and the benefit of Application No. PCT/JP2017/046789 filed on Dec. 26, 2017, each of which is hereby incorporated by reference in their entireties.

TECHNICAL FIELD

The present invention relates to a method for producing urolithins.

BACKGROUND ART

Urolithins, represented by urolithin A and urolithin C, are known to be metabolites of ellagic acid derived from, for example, ellagitannin contained in pomegranate, raspberry, blackberry, cloudberry, strawberry, walnut, and the like.

Ellagitannin is classified as a hydrolyzable tannin, and known to be hydrolyzed in the body after ingestion, to be converted into ellagic acid. Ellagic acid per se is also present in fruits and the like.

Regarding production of urolithins in the body, production of urolithins from ellagitannin such as geraniin in rat has been shown by analysis of urinary urolithins (Non-patent Document 1).

It has also been reported that, is human, urinary urolithins were detected following ingestion of a pomegranate extract containing ellagitannin composed mainly of punicalagin, and that urolithin A and urolithin C are major ellagic acid metabolites (Non-patent Document 2).

These urolithins are known to have a variety of physiological activities, and expected to be useful as materials of drugs, cosmetics, and foods and drinks.

For example, urolithin A has been reported to have functions such as antioxidant action (Non-patent Document 3), anti-inflammatory action (Non-patent Document 4), anti-glycation action (Non-patent Document 5), and mitophagy-promoting action (Non-patent Document 6), and therefore its development as a material having anti-aging function has been expected.

As an example of methods for synthesizing these urolithins, a method in which 2-bromo-5-methoxybenzoic acid as a starting material is demethylated to produce 2-bromo-5-hydroxybenzoic acid, and then reaction with resorcinol is performed to obtain urolithin A, has been reported (Non-patent Document 1). However, such a chemical synthesis method is not suitable for use of urolithins as materials of functional foods (including drinks and supplements).

It is known that ellagitannin and ellagic acid, after ingestion into the body, undergo metabolism by the intestinal microbial flora to be converted to urolithins. Recently, a microorganism belonging to *Gordonibacter urolithinfaciens* was isolated and identified as an intestinal bacterium that produces urolithin C, which is a urolithin, from ellagic acid, and a method for producing urolithin C by fermentation of ellagic acid using this intestinal bacterium has been reported (Patent Document 1, Non-patent Document 7), However, the accumulated concentration of urolithin C in the fermentation liquid was only about 2 mg/L, and urolithin A, which is a major ellagic acid metabolite in human, cannot be produced.

A microorganism belonging to *Gordonibacter pamelaeae*, which belongs to the genus *Gordonibacter*, has also been reported to produce urolithin C from ellagic acid. However, production of urolithin A has not been reported. No microorganism, including this microorganism, has been reported to be capable of eliminating the hydroxyl group at the 8-position of a urolithin to produce another kind of urolithin.

PRIOR ART DOCUMENTS

Patent Document

[Patent Document 1] WO 2014/147280

Non-Patent Documents

[Non-patent Document 1] J. Agric. Food Chem. 56, 393-400 (2008)
[Non-patent Document 2] Mol. Nutr. Food Res. 58, 1199-1211 (2014)
[Non-patent Document 3] Biosci. Biotechnol. Biochem. 76, 395-399 (2012)
[Non-patent Document 4] J. Agric. Food Chem. 60, 8866-8876 (2012)
[Non-patent Document 5] Mol. Nutr. Food Res. 55, S35-S43 (2011)
[Non-patent Document 6] Nature Medicine, 22, 879-888 (2016)
[Non-patent Document 7] Food Func., 5, 8, 1779-1784 (2014)

SUMMARY OF THE INVENTION

Problems to be Solved by the Invention

An object of the present invention is to provide a method for eliminating the hydroxyl group at the 8-position of a urolithin to produce another kind of urolithin. An object of the present invention is also to provide a novel method for producing urolithin B.

Means for Solving the Problems

In order to solve the problem described above, the present inventors intensively studied to discover a microorganism having an ability to eliminate the hydroxyl group at the 8-position of a urolithin to produce another kind of urolithin, thereby completing the present invention. The present invention is as follows.

[1] A method for producing a second urolithin represented by the following General Formula (2), comprising the following Step (a):

Step (a): allowing, in a solution containing a first urolithin represented by the following General Formula (1), a microorganism having an ability to produce the second urolithin represented by the following General Formula (2) from the first urolithin to produce the second urolithin from the first urolithin.

(1)

$$\begin{array}{c} R_4 \\ R_3 \end{array} \begin{array}{c} O \\ \end{array} \begin{array}{c} R_5 \\ OH \\ R_2 \quad R_1 \quad R_7 \quad R_6 \end{array}$$

(wherein $R_1$ to $R_7$ each represent a hydroxyl group, a hydrogen atom, or a methoxy group, and one or more of $R_1$ to $R_7$ represents a hydroxyl group)

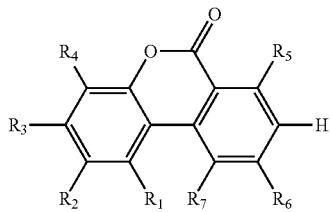

(2)

(wherein $R_1$ to $R_7$ are identical to the $R_1$ to $R_7$, respectively, of the first urolithin represented by the General Formula (1)).

[2] The production method according to [1], wherein the microorganism is a microorganism belonging to the genus *Slackia*.

[3] The production method according to [2], wherein the microorganism belonging to the genus *Slackia* is a microorganism belonging to *Slackia heliotrinireducens*.

[4] The production method according to [3], wherein the microorganism belonging to *Slackia heliotrinireducens* is the *Slackia heliotrinireducens* DSM 20476 strain.

[5] The production method according to any one of [1] to [4], wherein the first urolithin is urolithin C, and the second urolithin is isourolithin A.

[6] The production method according to [5], wherein the urolithin C is obtained by allowing, in a solution containing a raw material of urolithin C, a microorganism having an ability to produce urolithin C from the raw material of urolithin C to produce urolithin C from the raw material of urolithin C.

[7] The production method according to [5], further comprising the following Step (b1):

Step (b1): allowing, in a solution containing a raw material of urolithin C, a microorganism having an ability to produce urolithin C from the raw material of urolithin C to produce urolithin C from the raw material of urolithin C;

wherein the Step (a) and the Step (b1) are carried out in the same system.

[8] The production method according to [6] or [7], wherein the microorganism having an ability to produce urolithin C from the raw material of urolithin C is a microorganism belonging to the genus *Gordonibacter*.

The production method according to [8], wherein the microorganism belonging to the genus *Gordonibacter* is one or more selected from the group consisting of microorganisms belonging to *Gordonibacter pamelaeae*, microorganisms belonging to *Gordonibacter urolithinfaciens*, microorganisms belonging to and *Gordonibacter faecihominis*. [10] The production method according to [9], wherein the microorganism belonging to *Gordonibacter pamelaeae* is the *Gordonibacter pamelaeae* DSM 19378 strain.

[11] The production method according to [9] or [10], wherein the microorganism belonging to *Gordonibacter urolithinfaciens* is the *Gordonibacter urolithinfaciens* DSM 27213 strain.

[12] The production method according to any one of [9] to [11], wherein the microorganism belonging to *Gordonibacter faecihominis* is the *Gordonibacter faecihominis* JCM 16058 strain.

[13] The production method according to any one of [6] to [12], wherein the raw material of urolithin C is ellagic acid and/or ellagitannin.

[14] The production method according to any one of [1] to [4], wherein the first urolithin is urolithin A, and the second urolithin is urolithin B.

[15] The production method according to [14], wherein the urolithin A is obtained by allowing, in a solution containing a raw material of urolithin A, a microorganism having an ability to produce urolithin A from the raw material of urolithin A to produce urolithin A from the raw material of urolithin A.

[16] The production method according to [14], further comprising the following Step (b2):

Step (b2): allowing, in a solution containing a raw material of urolithin A, a microorganism having an ability to produce urolithin A from the raw material of urolithin A to produce urolithin A from the raw material of urolithin A;

wherein the Step (a) and the Step (b2) are carried out in the same system.

[17] The production method according to [15] or [16], wherein the microorganism having as ability to produce urolithin A from the raw material of urolithin A is a microorganism belonging to the genus *Clostridium*.

[18] The production method according to [17], wherein the microorganism belonging to the genus *Clostridium* is one or more selected from the group consisting of microorganisms belonging to *Clostridium bolteae*, microorganisms belonging to *Clostridium asparagiforme*, and microorganisms belonging to *Clostridium citroniae*.

[19] The production method according to [18], wherein the microorganism belonging to *Clostridium bolteae* is one or more selected from the group consisting of the *Clostridium bolteae* JCM 12243 strain, DSM 15670 strain, and DSM 29485 strain.

[20] The production method according to [18] or [19], wherein the microorganism belonging to *Clostridium asparagiforme* is the *Clostridium asparagiforme* DSM 15981 strain.

[21] The production method according to any one of [18] to [20], wherein the microorganism belonging to *Clostridium citroniae* is the *Clostridium citroniae* DSM 19261 strain.

[22] The production method according to any one of [15] to [21], wherein the raw material of urolithin A is urolithin C.

[23] The production method according to [22], wherein the urolithin C is obtained by allowing, in a solution containing a raw material of urolithin C, a microorganism having an ability to produce urolithin C from the raw material of urolithin C to Produce urolithin C from the raw material of urolithin C.

[24] The production method according to [22], further comprising the following Step (b21):

Step (b21): allowing, in a solution containing a raw material of urolithin C, a microorganism having an ability to produce urolithin C from the raw material of urolithin C to produce urolithin C from the raw material of urolithin C;

wherein the Step (a) and the Step (b21) are carried out in the same system.

[25] The production method according to [23] or [24], wherein the microorganism having an ability to produce urolithin C from the raw material of urolithin C is a microorganism belonging to the genus *Gordonibacter*.

[26] The production method according to [25], wherein the microorganism belonging to the genus *Gordonibacter* is one or more selected from the group consisting of microorganisms belonging to *Gordonibacter pamelaeae*, microorganisms belonging to *Gordonibacter urolithinfaciens*, and microorganisms belonging to *Gordonibacter faecihominis*.

[27] The production method according to [26], wherein the microorganism belonging to *Gordonibacter pamelaeae* is the *Gordonibacter pamelaeae* DSM 19378 strain.

[28] The production method according to [26] or [27], wherein the microorganism belonging to *Gordonibacter urolithinfaciens* is the *Gordonibacter urolithinfaciens* DSM 27213 strain.

[29] The production method according to any one of [26] to [28], wherein the microorganism belonging to *Gordonibacter faecihominis* is the *Gordonibacter faecihominis* JCM 16058 strain.

[30] The production method according to any one of [23] to [29], wherein the raw material of urolithin C is ellagic acid and/or ellagitannin.

[31] The production method according to any one of [1] to [30], wherein the Step (a) is carried out in an environment with a gas phase containing hydrogen.

[32] The production method according to [31], wherein the hydrogen contains hydrogen produced using formic acid and/or a salt thereof as a raw material(s).

[33] A method for producing urolithin B, comprising the following Steps (d) to (g):

Step (d): allowing, in a solution containing a raw material of urolithin C, a microorganism having an ability to produce urolithin C from the raw material of urolithin C to produce urolithin C from the raw material of urolithin C;

Step (e): allowing, in a solution containing urolithin C, a microorganism having an ability to produce isourolithin A from urolithin C to produce isourolithin A from urolithin C;

Step (f): inoculating a microorganism having an ability to produce urolithin B from isourolithin A, into a solution containing the isourolithin A produced in the Step (a); and Step (g): allowing, in the solution containing the isourolithin A after the Step (f), a microorganism having as ability to produce urolithin B from the isourolithin A to produce urolithin B from the isourolithin A;

wherein the Steps (d) to (g) are carried out in the same system.

[34] The production method according to [33], wherein the microorganism having an ability to produce urolithin C from the raw material of urolithin C is a microorganism belonging to the genus *Gordonibacter*, wherein the microorganism having an ability to produce isourolithin from urolithin s a microorganism belonging to the genus *Slackia*, and wherein the microorganism having an ability to produce urolithin B from isourolithin A is a microorganism belonging to the genus *Clostridium*.

[35] The production method according to [34], wherein the microorganism belonging to the genus *Slackia* is a microorganism belonging to *Slackia heliotrinireducens*.

[36] The production method according to [35], wherein the microorganism belonging to *Slackia heliotrinireducens* is the *Slackia heliotrinireducens* DSM 20476 strain.

[37] The production method according to any one of [34] to [36], wherein the microorganism belonging to the genus *Clostridium* is one or more selected from the group consisting of microorganisms belonging to *Clostridium bolteae*, microorganisms belonging to *Clostridium asparagiforme*, and microorganisms belonging to *Clostridium citroniae*.

[38] The production method according to [37], wherein the microorganism belonging to *Clostridium bolteae* is one or more selected from the group consisting of the *Clostridium bolteae* JCM 12243 strain, DSM 15670 strain, and DSM 29485 strain.

[39] The production method according to [37] or [38], wherein the microorganism belonging to *Clostridium asparagiforme* is the *Clostridium asparagiforme* DSM 15981 strain.

[40] The production method according to any one of [37] to [39], wherein the microorganism belonging to *Clotridium citroniae* the *Clostridium citroniae* DSM 19261 strain.

[41] The production method according to any one of [34] to [40], wherein the microorganism belonging to the genus *Gordonibacter* is one or more selected from the group consisting of microorganisms belonging to *Gordonibacter pamelaeae*, microorganisms belonging to *Gordonibacter urolithinfaciens*, and microorganisms belonging to *Gordonibacter faecihominis*.

[42] The production method according to [41], wherein the microorganism belonging to *Gordonibacter pamelaeae* is the *Gordonibacter pamelaeae* DSM 19378 strain.

[43] The production method according to [41] or [42], wherein the microorganism belonging to *Gordonibacter urolithinfaciens* is the *Gordonibacter urolithinfaciens* DSM 27213 strain.

[44] The production method according to any one of [41] to [43], wherein the microorganism belonging to *Gordonibacter faecihominis* is the *Gordonibacter faecihominis* JCM 16058 strain.

[45] The production method according to any one of [33] to [44], wherein the raw material of urolithin C is ellagic acid and/or ellagitannin.

Effect of the Invention

According to the present invention, a method for eliminating, from a urolithin having a hydroxyl group at the 8-position, the hydroxyl group at the 8-position to produce another kind of urolithin can be provided. According to the present invention, a method for producing urolithin B can be also provided. By using urolithins obtained by the production method for the present invention for cosmetics, quasi drugs, medical products, sanitary articles, drugs, foods and drinks (including supplements), and the like, production of effects such as antioxidant action, anti-inflammatory action, anti-glycation action, mitophagy-promoting action, and the like can be expected.

MODE FOR CARRYING OUT THE INVENTION

In the present description, the accession numbers of microbial strains beginning with the letters "DSM" are numbers given to microorganisms stored in DSMZ (Deutsche Sammlung von Mikroorganismen und Zellkulturen GmbH). The accession numbers of microbial strains beginning with the letters "JCM" are numbers given to microorganisms stored in the RIKEN Bioresource Center.

The present invention includes a method for producing a urolithin (first invention), a method for producing a food or drink containing a urolithin (second invention), a method for producing urolithin B (third invention), and a method for producing a food or drink containing urolithin B (fourth invention).

Table 1 shows specific examples of urolithins.

TABLE 1

Table 1. Types of Urolithins

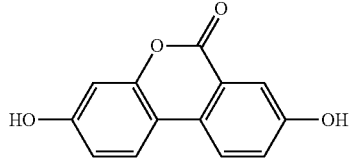

Urolithin A

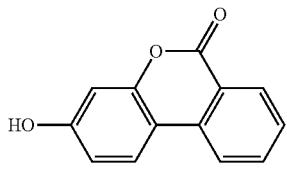 [SMILES: O=c1oc2cc(O)ccc2c2ccccc12]

Urolithin B

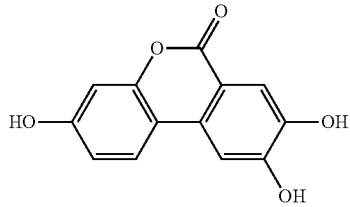 [SMILES: O=c1oc2cc(O)ccc2c2cc(O)c(O)cc12]

Urolithin C

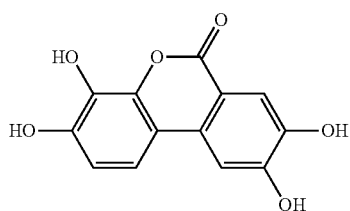 [SMILES: O=c1oc2c(O)c(O)ccc2c2cc(O)c(O)cc12]

Urolithin D

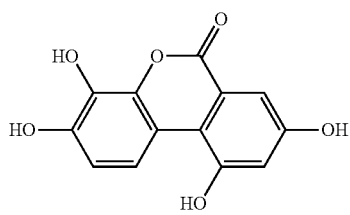 [SMILES: O=c1oc2c(O)c(O)ccc2c2c(O)cc(O)cc12]

Urolithin E

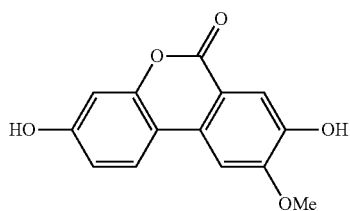 [SMILES: COc1cc2c(cc1O)c(=O)oc1cc(O)ccc12]

Urolithin M3

TABLE 1-continued

Table 1. Types of Urolithins

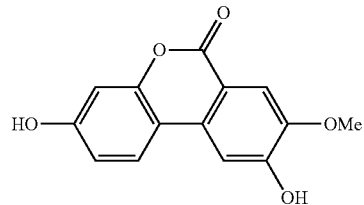 [SMILES: COc1cc2c(=O)oc3cc(O)ccc3c2cc1O]

Urolithin M4

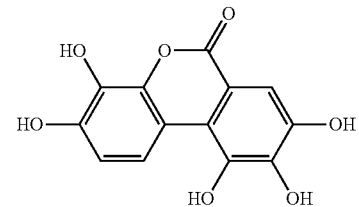 [SMILES: O=c1oc2c(O)c(O)ccc2c2c(O)c(O)c(O)cc12]

Urolithin M5

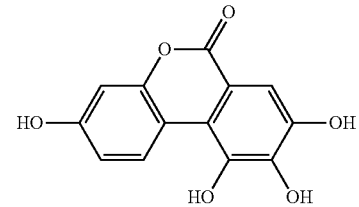 [SMILES: O=c1oc2cc(O)ccc2c2c(O)c(O)c(O)cc12]

Urolithin M6

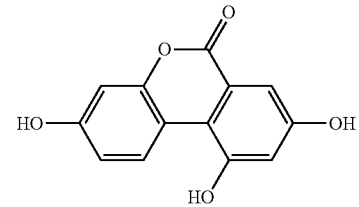 [SMILES: O=c1oc2cc(O)ccc2c2c(O)cc(O)cc12]

Urolithin M7

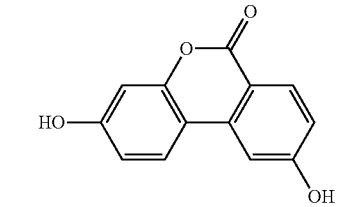 [SMILES: O=c1oc2cc(O)ccc2c2cc(O)ccc12]

Isourolithin A

1. Method for Producing Urolithin

The method for producing a urolithin as the first invention of the present invention includes the following Step (a), and the method may also include other steps.

(1) Step (a)

Step (a) is a step of allowing, in a solution containing a first urolithin represented by the following General Formula (1), a microorganism having an ability to produce a second urolithin represented by the following General Formula (2) from the first urolithin to produce the second urolithin from the first urolithin.

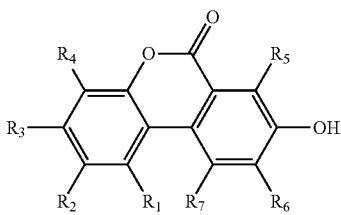

(1)

(wherein $R_1$ to $R_7$ each represent a hydroxyl group, a hydrogen atom, or a methoxy group, and one or more of $R_1$ to $R_7$ represents a hydroxyl group)

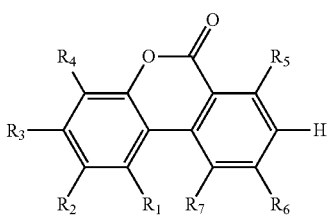

(2)

(wherein $R_1$ to $R_7$ are identical to the $R_1$ to $R_7$, respectively, of the first urolithin represented by the General Formula (I)).

Specific examples of the first urolithin include urolithin A, urolithin C, urolithin D, urolithin E, urolithin M3, urolithin M5, urolithin M6, and urolithin M7.

The second urolithin is the same as the first urolithin except that the hydroxyl group at the 8-position of the first urolithin is eliminated.

The first urolithin in the present invention is preferably urolithin C or urolithin A. In these cases, the second urolithin in the present invention is isourolithin A or urolithin B, respectively.

(Microorganism Having Ability to Produce Second Urolithin from First Urolithin)

The microorganism having an ability to produce the second urolithin from the first urolithin in the first invention of the present invention is not limited as long as it is a microorganism having an ability to produce the second urolithin from the first urolithin. The microorganism is preferably an anaerobic microorganism.

Specific examples of the microorganism include microorganisms belonging to the genus *Slackia*. More specifically, examples of the microorganism include microorganisms belonging to *Slackia heliotrinireducens*. Further more specifically, examples of the microorganism include *Slackia heliotrinireducens* DSM 20476 strain.

One or more of the above microorganisms may be used irrespective of the genus, the species, and the strain of each microorganism.

The microorganism having an ability to produce the second urolithin from the first urolithin in the first invention of the present invention is not limited to the same microbial strain as each deposited microbial strain described above, and may be substantially the same microbial strain as each deposited microbial strain. The substantially the same microbial strain means a microorganism whose base sequence of the 16S rRNA gene has a homology of not less than 97.5%, preferably not less than 98%, more preferably 99%, to the base sequence of the 16S rRNA gene of the deposited microbial strain. As long as the effect of the present invention is not deteriorated, the microorganism having an ability to produce the second urolithin from the first urolithin may be a microbial strain prepared by mutagenesis, genetic recombination, selection of a natural mutant strain, or the like from any of the deposited microbial strains, or from a microbial strain which is substantially the same as each deposited microbial strain.

(Resting Cells of Microorganism Having Ability to Produce Second Urolithin from First Urolithin)

The microorganism having an ability to produce the second urolithin from the first urolithin in the first invention of the present invention also includes resting cells thereof. The "resting cells" means cells prepared by removing medium components by an operation such as centrifugation from a cultured microorganism, and washing the resulting cells with water, salt solution such as physiological saline, or a buffer, followed by suspending the cells in the same liquid as the washing liquid, wherein the cells prepared are in a non-growing state. In the first invention of the present invention, the "resting cells" means cells at least having a metabolic system capable of producing the second urolithin from the first urolithin. The buffer is preferably phosphate buffer, Tris-HCl buffer, citrate-phosphate buffer, citrate buffer, MOPS buffer, acetate buffer, glycine buffer, or the like. The pH and the concentration of the buffer may be adjusted appropriately according to a conventional method.

(Solution Containing First Urolithin)

The solution containing the first urolithin in the first invention of the present invention is not limited as long as the microorganism having the ability to produce the second urolithin from the first urolithin can be allowed to produce the second urolithin from the first urolithin in the solution. The solution is preferably a medium, more preferably a medium described in the later-described. "Medium, and Production of Second Urolithin by Culture" section. In cases where the microorganism having the ability to produce the second urolithin from the first urolithin is resting cells, the above-described water, salt solution or buffer is preferred.

The "medium" as described in the present description means a solution containing a minimum medium and capable of allowing growth of the microorganism. The medium thus does not include a solution such as the above-described water, salt solution or buffer, which does not allow growth of the microorganism.

In cases where the first urolithin is added to the solution, it may be added either before or during the production of the second urolithin, and may be added at once, sequentially, or continuously.

The content of the first urolithin in the solution is usually not less than 0.01 g/L, preferably not less than 0.1 g/L, more preferably not less than 1 g/L. On the other hand, the content is usually not more than 100 g/L, preferably not more than 20 g/L, more preferably not more than 10 g/L.

(Medium, and Production of Second Urolithin by Culture)

In Step (a), the solution is preferably a medium. The medium is not limited, and examples of the medium include ANAEROBE BASAL BROTH (ABB medium), manufactured by Oxoid Limited; Wilkins-Chalgren Anaerobe Broth (CM0643), manufactured by Oxoid Limited; and GAM medium and modified GAM medium, manufactured by Nissui Pharmaceutical Co., Ltd.

These media are preferably supplemented with an inducer that induces an enzyme that produces the second urolithin from the first urolithin. Examples of the inducer include urolithins other than the first urolithin and the second urolithin, and precursors thereof; ellagic acid; and ellagitannin, which is a precursor of ellagic acid. One or more of the inducers may be used.

A water-soluble organic matter may also be added to the medium as a carbon source. Examples of the water-soluble organic matter include the following compounds: sugars such as glucose, arabinose, sorbitol, fructose, mannose, sucrose, trehalose, and xylose; alcohols such as glycerol; and organic acids such as valeric acid, butyric acid, propionic acid, acetic acid, formic acid, and fumaric acid.

The concentration of the organic matter added to the medium as a carbon source may be appropriately adjusted such that efficient growth is possible. In general, the amount of the organic matter added may be selected within the range of 0.1 to 10 wt/vol %.

In addition to the carbon source, a nitrogen source may be added to the medium. As the nitrogen source, various nitrogen compounds applicable to ordinary fermentation may be used.

Examples of preferred inorganic nitrogen sources include ammonium salts and nitrates, more preferably ammonium sulfate, ammonium chloride, ammonium phosphate, ammonium hydrogen phosphate, potassium nitrate, and sodium nitrate.

Examples of organic nitrogen sources include amino acids, yeast extracts, peptones (for example, polypeptone N), meat extracts (for example, Ehrlich bonito extract, Lab-Lemco powder, and bouillons), liver extracts, and digested serum powders.

In addition of the carbon source and the nitrogen source, inorganic compounds, for example, cofactors such as vitamins, and various salts, may be added to the medium to enhance the growth and the activity in some cases. Examples of inorganic compounds and vitamins as growth-aiding factors for microorganisms, derived from animals and plants include the following.

| Inorganic compounds | Vitamins |
|---|---|
| Potassium dihydrogen phosphate | Biotin |
| Magnesium sulfate | Folic acid |
| Manganese sulfate | Pyridoxine |
| Sodium chloride | Thiamine |
| Cobalt chloride | Riboflavin |
| Calcium chloride | Nicotinic acid |
| Zinc sulfate | Pantothenic acid |
| Copper sulfate | Vitamin B12 |
| Alum | Thioctic acid |
| Sodium molybdate | p-Aminobenzoic acid |
| Potassium chloride | |
| Boric acid and the like | |
| Nickel chloride | |
| Sodium tungstate | |
| Sodium selenate | |
| Ammonium ferrous sulfate | |
| Sodium acetate trihydrate | |
| Magnesium sulfate heptahydrate | |
| Manganese sulfate tetrahydrate | |

The growth can be improved in some cases by adding a reducing agent such as cysteine, cystine, sodium sulfate, sulfite, ascorbic acid, glutathione, thioglycolic acid, or rutin; or an enzyme that decomposes active oxygen species, such as catalase or superoxide dismutase, to the medium.

The gas phase and the aqueous phase during the culture preferably do not contain air or oxygen. For example, nitrogen and/or hydrogen is/are contained at an arbitrary ratio(s), or nitrogen and/or carbon dioxide is/are contained at an arbitrary ratio(s). The gas phase and the aqueous phase preferably contain hydrogen. From the viewpoint of promoting the production of the second urolithin, the ratio of hydrogen in the gas phase is usually not less than 0.5%, preferably not less than 1.0%, more preferably not less than 2.0%. On the other hand, the ratio is usually not more than 100%, preferably not more than 20%, more preferably not more than 10%.

The method for achieving such as environment of the gas phase and the aqueous phase during the culture is not limited. The method may be, for example, a method in which the gas phase is replaced with the above gas before the culture, a method in which, also during the culture, the above gas is further supplied from the bottom of the culture vessel, and/or supplied to the gas phase in the culture vessel, or a method is which the aqueous phase is bubbled with the above gas before the culture. As the hydrogen, hydrogen gas may be used as it is. Alternatively, a material(s) of hydrogen such as formic acid and/or a salt thereof may be added to the medium to allow production of hydrogen by an action of the microorganism during the culture.

The aeration rate is, for example, 0.005 to 2 vvm. An aeration rate of 0.05 to 0.5 vvm is preferred. The gas to be mixed may also be supplied as nanobubbles.

The culture temperature is preferably 20° C. to 45° C., more preferably 25° C. to 40° C., still more preferably 30° C. to 37° C.

The pressure condition of the culture vessel is not limited as long as the condition allows the growth. The pressure condition is, for example, within the range of 0.001 to 1 MPa, preferably 0.01 to 0.5 MPa.

The culture period is, for example, usually 8 to 340 hours, preferably 12 to 170 hours, more preferably 16 to 120 hours.

Production of the second urolithin can be promoted in some cases by addition of a surfactant, adsorbent, inclusion compound, or the like to the culture liquid.

Examples of the surfactant include TWEEN-80, which may be added at about 0.001 g/L to 10 g/L.

Examples of the adsorbent include cellulose and derivatives thereof; dextrin; the DIAION HP series and the SEPABEADS series, which are hydrophobic adsorbents manufactured by Mitsubishi Chemical Corporation; and the XAD series, manufactured by Organo Corporation.

Examples of the inclusion compound include α-cyclodextrin, β-cyclodextrin, γ-cyclodextrin, and cluster dextrin (highly branched cyclic dextrin). Among these, γ-cyclodextrin is most effective in some cases. By allowing coexistence of two or more kinds of inclusion compounds, the production of the second urolithin can be further promoted in some cases.

The total amount of the inclusion compound(s) to be added in terms of the molar ratio to the first urolithin is usually not less than 0.1 equivalents, preferably not less than equivalents, more preferably not less than 1.0 equivalent. On the other hand, the total amount is usually not more than 5.0 equivalents, preferably not more than 2.5 equivalents, more preferably not more than 2.0 equivalents.

(Production of Second Urolithin by Resting Cells)

In cases where the microorganism having the ability to produce the second urolithin from the first urolithin is resting cells, the solution is preferably water, a salt solution or a buffer described in the "Resting Cells of Microorganism Having Ability to Produce Second Urolithin from First Urolithin" section, rather than the medium. Regarding other conditions, the descriptions in the "Medium, and Production Second Urolithin by Culture" section are applied.

(First Urolithin)

The first urolithin in the first invention of the present invention may be prepared by any method. For example, the first urolithin may be synthesized by a chemical synthesis method or a fermentation method. In cases where the second urolithin produced by the first invention of the present invention is used as a food or drink, the first urolithin to be used therefor is preferably prepared by a fermentation method or an enzyme method using a food or drink or a material of a food or drink as a raw material.

Examples of the chemical synthesis method include a method described in Non-patent Document 1.

Examples of the fermentation method include a method in which a microorganism having an ability to produce the first urolithin from a raw material of the first urolithin is allowed, in a solution containing the raw material of the first urolithin, to produce the first urolithin from the raw material of the first urolithin.

(Steps that May be Included Before Step (a))

After the production of the first urolithin by the fermentation method, the first urolithin may be separated and/or purified for application to Step (a) as the first urolithin of Step (a). Alternatively, without performing the separation and/or the purification, the solution containing the first urolithin may be applied, as it is or after dilution or concentration, to Step (a) as the first urolithin of Step (a).

That is, the first invention of the present invention may include, before the Step (a), the following Steps (pre-a1) and (pre-a2) in this order, or may include the following Steps (pre-a1) and (pre-a3) in this order, as steps to be carried out in a system that is separate from the system in which the Step (a) is carried out.

Step (pre-a1): allowing, in a solution containing a raw material of the first urolithin, a microorganism having an ability to produce the first urolithin from the raw material of the first urolithin to produce the first urolithin from the raw material of the first urolithin.

Step (pre-a2): separating and/or purifying the first urolithin produced in Step (pre-a1), and applying the separated and/or purified first urolithin to Step (a) as the first urolithin of Step (a).

Step (pre-a3): applying the solution containing the first urolithin produced in Step (pre-a1), as it is or after dilution or concentration, to Step (a) as the first urolithin of Step (a).

(2) Step (b)

In the method for producing a urolithin as the first invention of the present invention, the following Step (b) is preferably included in addition to the Step (a), and the Step (a) and the Step (b) are preferably carried out in the same system.

Step (b): allowing, in a solution containing a raw material of the first urolithin, a microorganism having an ability to produce the first urolithin from the raw material of the first urolithin to produce the first urolithin from the raw material of the first urolithin.

(Same System)

The term "Step (a) and Step (b) are carried out in the same system" means that the series of processes from the production of the first urolithin in Step (b) from the raw material of the first urolithin by the microorganism having the ability to produce the first urolithin from the raw material of the first urolithin in the solution containing the raw material of the first urolithin, to the production of the second urolithin in Step (a) by the use of the resulting first urolithin as it is as the first urolithin of Step (a), is carried out continuously is the same system. That is, the term means that, for example, a step of separating and/or purifying the first urolithin produced in Step (b) is not included between Step (b) and Step (a).

More specifically, for example, the microorganism having the ability to produce the first urolithin from the raw material of the first urolithin and the microorganism having the ability to produce the second urolithin from the first urolithin are inoculated to the same culture liquid, and then cultured to produce the second urolithin. These microorganisms may be either the same kind microorganism or different kinds of microorganisms.

In cases where the first urolithin is urolithin C, the Step (b) is read as Step (b1). In cases where the first urolithin is urolithin A, the Step (b) is read as Step (b2)

In cases where the first urolithin is urolithin A, and the raw material of urolithin A is urolithin C, the Step (b) is read as Step (b21).

(Raw Material of First Urolithin)

The raw material of the first urolithin may be prepared by any method. This also applies to a raw material of the raw material of the first urolithin, a raw material of the former raw material, and further raw materials.

For example, such raw materials may be synthesized by a chemical synthesis method or a fermentation method. In cases where the second urolithin produced by the first invention of the present invention is used as a food or drink, the raw material of the first urolithin to be used therefor is preferably obtained by a fermentation method or an enzyme method.

Examples of the chemical synthesis method include a method described in Non-patent Document 1.

Examples of the fermentation method include a method in which the microorganism having the ability to produce the raw material of the first urolithin from a raw material of the raw material of the first urolithin is allowed, in a solution containing the raw material of the raw material of the first urolithin, to produce the raw material of the first urolithin from the raw material of the raw material of the first urolithin.

(Other Steps)

The first invention of the present invention may include the following steps.

The first invention of the present invention may include, for example, a step of quantifying the second urolithin obtained. The quantification method may be carried out according to a conventional method. For example, ethyl acetate to which an acid such as formic acid is added as required is added to the culture liquid, and the resulting mixture is then vigorously stirred, followed by centrifugation and then removal of the ethyl acetate phase. The same operation is carried out several times as required, and the resulting ethyl acetate phases are combined together to obtain a urolithin extract. The extract is then concentrated and dried under reduced pressure using an evaporator or the like, and dissolved in methanol. The resulting solution is filtered through a membrane such as a polytetrafluoroethylene (PTFE) membrane to remove insoluble matters, and then subjected to quantification by high-performance liquid chromatography. Examples of the conditions for the high-performance liquid chromatography include, but are not limited to, the following.

[Conditions for the High-Performance Liquid Chromatography]

Column: INERTSIL ODS-3 (250×4.6 mm) (manufactured by GL Science)

Eluent: water/acetonitrile/acetic acid=74/25/1

Flow rate: 1.0 mL/min

Column temperature: 40° C.

Detection: 305 nm

The first invention of the present invention may include a step of collecting the second urolithin obtained by the above step. The step of collecting includes a purification step or a concentration step. As the purification treatment in the purification step, a treatment such as sterilization of the microorganism by heat or the like; elimination of the microorganism by microfiltration (MF), ultrafiltration (UF), or the liken removal of solid matters and macromolecular substances; extraction with an organic solvent or an ionic liquid; or adsorption or decoloration using a hydrophobic adsorbent, ion-exchange resin, activated carbon column, or the like; may be carried out. Examples of the concentration treatment in the concentration step include concentration using an evaporator, reverse osmosis membrane, or the like.

The solution containing the second urolithin may be pulverized by freeze-drying, spray drying, or the like. In the pulverization, an excipient such as lactose, dextrin, or corn starch may be added.

1-1. One Preferred Embodiment

One preferred embodiment of the present invention is described below.

The present embodiment is a mode in which the first urolithin is urolithin C; the second urolithin is isourolithin A; and the microorganism having the ability to produce the second urolithin from the first urolithin is a microorganism belonging to the genus *Slackia*.

That is, the present embodiment is a method for producing isourolithin A, including the following Step (a1).

Step (a1): allowing, in a solution containing urolithin C, a microorganism belonging to the genus *Slackia* having an ability to produce isourolithin A from urolithin C to produce isourolithin A from urolithin C.

(Raw Material of Urolithin C)

Examples of the raw material of the urolithin C include ellagic acid; ellagitannins such as punicalagin and geraniin, which are precursors of the ellagic acid; and urolithin M5, and urolithin D and urolithin M6, which are precursors of urolithin C. The raw material of urolithin C is preferably ellagic acid and/or ellagitannin.

The plant from which the ellagic acid and/or the ellagitannin is/are produced not limited, and examples of the plant include pomegranate, raspberry, blackberry, cloudberry, boysenberry, strawberry, walnut, and geranium herb. Among these, pomegranate, boysenberry, and geranium herb are preferred since these contain large amounts of ellagic acid and/or ellagitannin. Pomegranate is more preferred.

The raw material of urolithin C is not limited as long as the microorganism having the ability to produce urolithin C from the raw material of urolithin C can be allowed to produce urolithin C from the raw material of urolithin C in a solution containing the raw material of urolithin C. One or more raw materials may be used.

(Microorganism Having Ability to Produce Urolithin C)

In the present embodiment, the microorganism having the ability to produce urolithin C from the raw material of urolithin C is not limited. For example, microorganisms belonging to the genus *Gordonibacter* and microorganisms belonging to the genus *Eggerthella* are preferred.

Among the microorganisms belonging to the genus *Gordonibacter*, microorganisms belonging to *Gordonibacter pamelaeae*, microorganisms belonging to *Gordonibacter urolithinfaciens*, microorganisms belonging to *Gordonibacter faecihominis* are more preferred.

Among the microorganisms belonging to *Gordonibacter pamelaeae*, the DSM 19378 strain is still more preferred. Among the microorganisms belonging to *Gordonibacter urolithinfaciens*, the DSM 27213 strain is still more preferred. Among the microorganisms belonging to *Gordonibacter faecihominis*, the JCM 16058 strain is still more preferred.

Among the microorganisms belonging to the genus *Eggerthella*, microorganisms belonging to *Eggerthella* sp. are preferred. The DC 3563 (NITE BP-02376) strain is more preferred.

One or more of the above microorganisms may be used irrespective of the genus, the species, and the strain of each microorganism.

The DC 3563 (NITE BP-02376) strain has been deposited to NITE Patent Microorganisms Depositary, National Institute of Technology and Evaluation [address: #122, 2-5-8 Kazusakamatari, Kisarazu-shi, Chiba 292-0818, Japan] as of Nov. 11, 2016 as international deposition in accordance with the Budapest Treaty.

(Resting Cells of Microorganism Having Ability to Produce Urolithin C)

The microorganism having the ability to produce urolithin C includes resting cells thereof. Regarding the resting cells, the descriptions in "Resting Cells of Microorganism Having Ability to Produce Second Urolithin from First Urolithin" are applied.

(Solution Containing Raw Material of Urolithin C)

The solution containing the raw material of urolithin C is not limited as long as the microorganism having the ability to produce urolithin C from the raw material of urolithin C can be allowed to produce urolithin C from the raw material of urolithin C in the solution. The solution is preferably a medium, more preferably a medium in the above-described "Medium, and Production of Second Urolithin by Culture" section. In cases where the microorganism is resting cells, the above-described water, salt solution or buffer is preferred.

The content of the raw material of urolithin C in the solution is usually not less than 0.01 g/L, preferably not less than 0.1 g/L, more preferably not less than 1.0 g/L. On the other hand, the content is usually not more than 100 g/L, preferably not more than 20 g/L, more preferably not more than 10 g/L.

(Medium, and Production of Urolithin C by Culture)

In cases where the microorganism having the ability to produce urolithin C from the raw material of urolithin C is allowed to produce urolithin C from the raw material of urolithin C in the solution containing the raw material of urolithin C, the solution is preferably a medium. Regarding details of more preferred media, culture conditions, and the like, the descriptions in the "Medium, and Production of Second Urolithin by Culture" section are applied.

Similarly to the cases described above, the production of urolithin C can be promoted in some cases by addition of a surfactant, adsorbent, inclusion compound, or the like to the culture liquid. Examples of the inclusion compound include α-cyclodextrin, β-cyclodextrin, γ-cyclodextrin, and cluster dextrin (highly branched cyclic dextrin). γ-Cyclodextrin is most effective, and α-cyclodextrin and β-cyclodextrin are also effective. By allowing coexistence of two or more kinds of inclusion compounds, the production of urolithin C can be further promoted in some cases.

The total amount of the inclusion compound(s) to be added in terms of the molar ratio to the total amount of the raw material of urolithin C is usually not less than 0.2 equivalents, preferably not less than equivalent, more preferably not less than 2.0 equivalents. On the other hand, the total amount of the inclusion compound(s) is usually not more than 10.0 equivalents, preferably not more than 5.0 equivalents, more preferably not more than 4.0 equivalents.

(Production of Urolithin C by Resting Cells)

In cases where the microorganism having the ability to produce urolithin C from the raw material of urolithin C is resting cells, the solution is preferably water, a salt solution or a buffer described in the "Resting Cells of Microorganism Having Ability to Produce Second Urolithin from First Urolithin" section, rather than a medium. Regarding other conditions, the descriptions in the "Medium, and Production of Second Urolithin by Culture" section are applied.

1-2. One Preferred Embodiment

Another preferred embodiment of the present invention is described below.

The present embodiment is a mode is which the first urolithin is urolithin A; the second urolithin is urolithin B; and the microorganism having the ability to produce the second urolithin from the first urolithin is a microorganism belonging to the genus *Slackia*.

That is, the present embodiment is a method for producing urolithin B, including the following Step (a2).

Step (a2): allowing, in a solution containing urolithin A, a microorganism belonging to the genus *Slackia* having an ability to produce urolithin B from urolithin A to produce urolithin B from urolithin A.

The urolithin A may be prepared by any method.

Examples of the raw material of the urolithin A include ellagic acid; and ellagitannins such as punicalagin and geraniin, which are precursors of the ellagic acid; and urolithin M7 and urolithin C, which are precursors of the urolithin A.

For example, in cases where urolithin C is used as the raw material of urolithin A, urolithin A obtained by a method for producing urolithin A, including a step of allowing a microorganism having an ability to produce urolithin A from urolithin C to produce urolithin A from urolithin C in a solution containing urolithin C may be used.

The microorganism having an ability to produce urolithin A from urolithin C is not limited as long as it is a microorganism having an ability to produce urolithin A from urolithin C. The microorganism is preferably an anaerobic microorganism.

Specific examples of the microorganism include microorganisms belonging to the genus *Clostridium*. More specifically, examples of the microorganism include microorganisms belonging to *Clostridium bolteae*, microorganisms belonging to *Clostridium asparagiforme*, and microorganisms belonging to *Clostridium citroniae*.

Examples of the microorganisms belonging to *Clostridium bolteae* include the DSM 29485 strain, DSM 15670 strain, and JCM 12243 strain.

Examples of the microorganisms belonging to *Clotridium asparagiforme* include the DSM 15981 strain.

Examples of the microorganisms belonging to *Clostridium citroniae* include the DSM 19261 strain.

One or more of the above microorganisms may be used irrespective of the genus, the species, and the strain of each microorganism.

Regarding other conditions, including the cases where urolithin C is obtained by allowing, in a solution containing a raw material of urolithin C, a microorganism having an ability to produce urolithin C from the raw material of urolithin C to produce urolithin C from the raw material of urolithin C, the above-described mode for urolithin C in the method for producing isourolithin A, including Step (a1) is applied.

2. Method for Producing Food or Drink Containing Second Urolithin

The method for producing a food or drink containing the second urolithin as the second invention of the present invention includes the above Step (a) and the following Step (c), and may also include other steps. The food or drink to be produced by the second invention of the present invention includes supplements. The supplements are classified into a group of food or drink composed of dietary supplements.

(1) Step (a)

Regarding Step (a), the above descriptions for the Step (a) in the first invention of the present invention are applied.

(2) Step (c)

Step (c) is a step of mixing the second urolithin produced in the Step (a) with a raw material of a food or drink to provide the food or drink. The food or drink is produced according to a conventional method by mixing an ordinary raw material of the food or drink with the second urolithin produced in the Step (a), and the timing of the mixing is not limited. Examples of the raw material of the food or drink include food additives. Further, if necessary, the resulting food or drink may be enclosed in an appropriate container such as a bottle, bag, can, box, or pack.

The food or drink produced by the second invention of the present invention may contain, as a major component, water, protein, carbohydrate, lipid, vitamin, mineral, organic acid, organic base, juice, flavor, or the like.

Examples of the protein include animal and plant proteins such as whole milk powder, skimmed milk powder, semi-skimmed milk powder, casein, soy protein, chicken egg protein, and meat protein; hydrolysates thereof, and butter.

Examples of the carbohydrate include sugars, processed starches (dextrin, soluble starch, British starch, oxidized starch, starch ester, starch ether, and the like), and dietary fibers.

Examples of the lipid include lard; and vegetable oils and fats such as safflower oil, corn oil, rapeseed oil, and palm oil, and fractionated oils, hydrogenated oils, and transesterified oils thereof.

Examples of the vitamin include vitamin A, carotenes, vitamin Bs, vitamin C, vitamin Ds, vitamin E, vitamin Ks, vitamin P, vitamin Q, niacin, nicotinic acid, pantothenic acid, biotin, inositol, choline, and folic acid.

Examples of the mineral include calcium, potassium, magnesium, sodium, copper, iron, manganese, zinc, selenium, and whey minerals.

Examples of the organic acid include malic acid, citric acid, lactic acid, and tartaric acid.

Two or more of these components may be used in combination. These components may be synthetic products.

The content of the second urolithin produced in the Step (a) with respect to the total amount of the food or drink produced by the second invention of the present invention is not limited. The content is preferably a content with which an effect of the second urolithin such as antioxidant action, anti-inflammatory action, anti-glycation action, mitophagy-promoting action, or the like can be obtained by ingestion of the food or drink.

The content of the second urolithin with respect to the total amount of the food or drink is usually not less than 0.0001% by mass, preferably not less than 0.001% by mass, more preferably not less than 0.01% by mass. The content is usually not more than 10% by mass, preferably not more than 1% by mass, more preferably not more than 0.1% by mass.

In cases where the food or drink is a supplement, it may be in any form such as a solid matter, gel-like product, or liquid product. Examples of the form include various processed foods and drinks, powders, tablets, balls, capsules, jellies, and granules. Further, necessary, the supplement may be enclosed in an appropriate container such as a bottle, bag, can, box, or pack.

The supplement may contain an additive, and examples of the additive include excipients such as dextrin; preservatives such as vitamin C; corrigents such as vanillin; dyes such as safflower dye; monosaccharides, oligosaccharides, and polysaccharides (for example, glucose, fructose, sucrose, saccharose, and carbohydrates containing these); acidulants; perfumes; fats and oils; emulsifiers; whole milk powder; and agar. Two or more of these components may be used in combination. These components may be synthetic products.

3. Method for Producing Urolithin B

The method for producing urolithin B according to the third invention of the present invention includes the following Steps (d) to (g) which are carried out in the same system.

(1) Step (d)

Step (d) is a step of allowing, in a solution containing a raw material of urolithin C, a microorganism having an ability to produce urolithin C from the raw material of urolithin C to produce urolithin C from the raw material of urolithin C.

(2) Step (e)

Step (e) is a step of allowing, in a solution containing urolithin C, a microorganism having an ability to produce isourolithin A from urolithin C to produce isourolithin A from urolithin C.

Regarding Steps (d) and (e), the case where the first urolithin is urolithin C, and the second urolithin is isourolithin A, in the first invention of the present invention is applied.

(3) Step (f)

Step (f) is a step of inoculating a microorganism having an ability to produce urolithin a from isourolithin A, into a solution containing the isourolithin A produced in the Step (e).

(Inoculation)

The method for inoculating a microorganism having an ability to produce urolithin B from isourolithin A, into a solution containing the isourolithin A produced in the Step (e) may be carried out according to a conventional method.

The timing of inoculating the microorganism having an ability to produce urolithin B from isourolithin A, into a solution containing the isourolithin A produced in the Step (e) is not limited as long as the solution contains the isourolithin A. Usually, the inoculation is carried out at a timing when the molar yield of the isourolithin A produced is 10 to 100%, preferably 20 to 100%, more preferably 40 to 100%, with respect to the raw material of urolithin C added. The molar yield of the isourolithin A produced in the solution may be measured by a conventional method after sampling part of the solution. Thus, the present step may include a step of sampling part of the solution, and measuring the molar yield of the isourolithin A produced. Usually, the inoculation into the solution is carried out once. However, the inoculation may be carried out a plurality of times.

(Microorganism Having Ability to Produce Urolithin B from Isourolithin A)

In the present step, the microorganism having an ability to produce urolithin B from isourolithin A is not limited as long as it is a microorganism having an ability to produce urolithin B from isourolithin A. The microorganism is preferably an anaerobic microorganism.

Specific examples of the microorganism include microorganisms belonging to the genus *Clostridium*. More specifically, examples of the microorganism include microorganisms belonging to *Clostridium bolteae*, microorganisms belonging to *Clostridium asparagiforme*, and microorganisms belonging to *Clostridium citroniae*.

Examples of the microorganisms belonging to *Clostridium bolteae* include the DSM 29485 strain, DSM 15670 strain, and JCM 12243 strain.

Examples of the microorganisms belonging to *Clostridium asparagiforme* include the DSM 15981 strain.

Examples of the microorganisms belonging to *Clostridium citroniae* include the DSM 19261 strain.

One or more of the above microorganisms may be used irrespective of the genus, the species, and the strain of each microorganism.

The microorganism having an ability to produce urolithin B from isourolithin A in the present step is not limited to the same microbial strain as each deposited microbial strain described above, and may be substantially the same microbial strain as each of the DSM 29485 strain, DSM 15670 strain, JCM 12243 strain, DSM 15981 strain, and DSM 19261 strain. The substantially the same microbial strain means a microorganism whose base sequence of the 16S rRNA gene has a homology of not less than 97.5%, preferably not less than 98%, more preferably 99%, to the base sequence of the 16S rRNA gene of each microbial strain described above. As long as the effect of the present invention is not deteriorated, the microorganism having an ability to produce urolithin B from isourolithin A may be a microbial strain prepared by mutagenesis, genetic recombination, selection of a natural mutant strain, or the like from any of the microbial strains, or from a microbial strain which is substantially the same as any of the microbial strains.

(Resting Cells of Microorganism Having Ability to Produce Urolithin B from Isourolithin A)

The microorganism having an ability to produce urolithin B from isourolithin A includes its resting cells. Regarding the resting cells, the description for the case where the first urolithin is urolithin C, and the second urolithin is isourolithin A, in the section "Resting Cells of Microorganism Having Ability to Produce Second Urolithin from First Urolithin" for the first invention of the present invention is applied.

(Solution Containing Isourolithin A)

The solution containing isourolithin A means a solution containing the isourolithin A produced in the Step (e).

In cases where additional isourolithin A is added to the solution separately from the isourolithin A produced in the Step (e), it may be added either before or during the production of urolithin B, at once, sequentially, or continuously.

The content of the isourolithin A in the solution is usually not less than 0.01 g/L, preferably not less than 0.1 g/L, more preferably not less than 1 g/L. On the other hand, the content is usually not more than 100 g/L, preferably not more than 20 g/L, more preferably not more than 10 g/L.

(4) Step (g)

The Step (g) is a step of allowing, in the solution containing isourolithin A after the Step (f), a microorganism having an ability to produce urolithin B from the isourolithin A to produce urolithin B from the isourolithin A.

In the present step, the microorganism having an ability to produce urolithin B from the isourolithin the microorganism in the Step (f) having an ability to produce urolithin B from isourolithin A inoculated into the solution containing the isourolithin A produced in the Step (e). Thus, regarding this microorganism, the description in the section "Microorganism Having Ability to Produce Urolithin B from isourolithin A" for the Step (f) is applied.

In the present step, the microorganism having an ability to produce urolithin B from isourolithin A includes its resting cells. Regarding the resting cells, the description in the section "Resting Cells of Microorganism Having Ability to Produce Urolithin B from Isourolithin A" for the Step is applied.

(Medium, and Production of Urolithin B by Culture)

In the method for producing urolithin B according to the third invention of the present invention, the Step (d) to Step (g) are carried out in the same system. Thus, regarding the culture medium conditions, and the conditions for producing urolithin B by the culture in the present step, the description for the case where the first urolithin is urolithin C, and the second urolithin is isourolithin A, in the section "Medium, and Production of Second Urolithin by Culture" for the first invention of the present invention applied to Step (d) is applied.

(Production of Urolithin B by Resting Cells)

In the method for producing urolithin B according to the third invention of the present invention, the Step (d) to Step (g) are carried out in the same system. Thus, the water, salt solutions, and buffers described in the section "Resting Cells of Microorganism Having Ability to Produce Second Urolithin from First Urolithin" for the first invention of the present invention applied to Step (d) are preferred rather than the medium.

(Same System)

The term "Steps (d) to (g) are carried out in the same system" means that the series of the following processes is continuously carried out in the same system: Step (d), in which urolithin C is produced from a raw material of urolithin C by a microorganism having an ability to produce urolithin C from the raw material of urolithin C is a solution containing the raw material of urolithin C; Step (e); Step (f); and then Step (g), in which urolithin B is produced. Thus, the term means that no separation and/or purification of a product(s) (that is, urolithin C and/or isourolithin A) is carried out between any of Step (d), Step (e), Step (f), and Step (g).

(Other Steps)

The third invention of the present invention may include the following steps.

The third invention of the present invention may include, for example, a step of quantifying or a step of recovering the urolithin B obtained. Regarding these steps, the description in the section "Other Steps" for the first invention of the present invention is applied.

4. Method for Producing Food or Drink Containing Urolithin B

The method for producing a food or drink containing urolithin B as the fourth invention of the present invention includes the above Step (d) to Step (g) which are carried out in the same system and the following Step (h), and may also include other steps. The food or drink to be produced by the fourth invention of the present invention includes supplements. The supplements are classified into a group of food or drink composed of dietary supplements.

(1) Step (d) to Step (g) Carried Out in Same System

Regarding Step (d) to Step (g) carried out in the same system, the description for Step (d) to Step (g) carried out in the same system in the third invention of the present invention is applied.

(2) Step (h)

Step (h) is a step of mixing the urolithin B produced in Step (d) to Step (g) carried out in the same system, with a raw material of a food or drink to provide the food or drink.

Regarding Step (h), the description for Step (c) in the third invention of the present invention is applied.

EXAMPLES

The present invention is described below in more detail by way of specific examples. However, the present invention is not limited to these examples.

Example 1

Production of Isourolithin A from Urolithin C 10 mL or ABB medium (manufactured by Oxoid Limited) containing 0.8 g/L of urolithin C was heat-sterilized by autoclaving at 121° C. for 15 minutes, and the gas phase was replaced with $N_2:CO_2:H_2$ (80%/10%/10%) gas. To this medium, the *Slackia heliotrinireducens* DSM 20476 strain was inoculated, and anaerobic culture was performed at 37° C. After completion of the culture, the same amount of ethyl acetate was added to 5 ml of the culture liquid to extract urolithin, and the resulting ethyl acetate phase was concentrated under reduced pressure, followed by drying. The thus obtained dried product was redissolved in 0.5 ml of methanol, and quantitative analysis of urolithin was carried out by HPLC.

The HPLC was carried out under the following conditions. Urolithins manufactured by DALTON PHARMA, after dissolution in DMSO, were used as standard samples. As a result of 2 weeks of the culture, as shown in Table 2, isourolithin A was obtained at a molar yield of 22.5% with respect to the urolithin C added.

<HPLC Analysis Conditions>

Column: INERTSIL ODS-3 (250×4.6 mm) (manufactured by GL Science)
Fluent: water/acetonitrile/acetic acid=74/25/1
Flow rate: 1.0 mL/min
Column temperature: 40° C.
Detection: 305 nm

TABLE 2

| Microorganism | Substrate | Product |
| --- | --- | --- |
| *Slackia Heliotrinireducens* DSM 20476 strain | Urolithin C 0.8 g/L | Isourolithin A 0.170 g/L (molar yield, 22.5%) |

Example 2

Production of Isourolithin A from Ellagic Acid

Into ABB medium (manufactured by Oxoid Limited) containing 1.0 g/L ellagic acid, the *Slackia heliotrinireducens* DSM 20476 strain, and the *Gordonibacter pamelaeae* DSM 19378 strain, the *Gordonibacter urolithinfaciens* DSM 27213 strain or the *Gordonibacter faecihominis* JCM 16058 strain were inoculated, and culture was performed in the same manner as in Example 1. As a result of 4 days of the culture, as shown in Table 3, isourolithin A was obtained at molar yields of 62.3%, 55.9%, and 7.4%, respectively, with respect to the ellagic acid added.

TABLE 3

| Microorganism | Substrate Ellagic Acid | Product Isourolithin A |
| --- | --- | --- |
| *Slackia heliotrinireducens* DSM 20476 strain and *Gordonibacter pamelaeae* DSM 19378 strain | 1.0 g/L | 0.469 g/L (molar yield, 62.3%) |
| *Slackia heliotrinireducens* DSM 20476 strain and *Gordonibacter urolithinfaciens* DSM 27213 strain | 1.0 g/L | 0.422 g/L (molar yield, 55.9%) |
| *Slackia heliotrinireducens* DSM 20476 strain and *Gordonibacter faecihominis* JCM 16058 strain | 1.0 g/L | 0.056 g/L (molar yield, 7.4%) |

Example 3

Production of Urolithin B from Urolithin C

Into ABB medium (manufactured by Oxoid Limited) containing 0.8 g/L urolithin C, the *Slackia heliotrinireducens* DSM 20476 strain, and the *Clostridium bolteae* JCM 12243 strain, the *Clostridium asparagiforme* DSM 15981 strain or the *Clostridium citroniae* DSM 19261 strain were inoculated, and culture was performed in the same manner as in Example 1. As a result of 2 weeks of the culture, as shown in Table 4, urolithin B was obtained at molar yields of 0.69%, 0.63%, and 0.46%, respectively, with respect to the urolithin C added.

TABLE 4

| Microorganism | Substrate Urolithin C | Product Urolithin B |
| --- | --- | --- |
| *Slackia heliotrinireducens* DSM 20476 strain and *Clostridium bolteae* JCM 12243 strain | 0.8 g/L | 0.005 g/L (molar yield, 0.69%) |
| *Slackia heliotrinireducens* DSM 20476 strain and *Clostridium asparagiforme* DSM 15981 strain | 0.8 g/L | 0.004 g/L (molar yield, 0.63%) |
| *Slackia heliotrinireducens* DSM 20476 strain and *Clostridium citroniae* DSM 19261 strain | 0.8 g/L | 0.003 g/L (molar yield, 0.46%) |

Example 4

Production of Urolithin B from Ellagic Acid

Into ABB medium (manufactured by Oxoid Limited) containing 1.0 g/L ellagic acid, the *Slackia heliotrinireducens* DSM 20476 strain, the *Gordonibacter pamelaeae* DSM 19378 strain and the *Clostridium bolteae* JCM 12243 strain were inoculated, and culture was performed in the same manner as in Example 1. As a result of 2 weeks of the culture, as shown in Table 5, urolithin B was obtained at molar yields of 5.3%, with respect to the ellagic acid added.

TABLE 5

| Microorganism | Substrate | Product |
| --- | --- | --- |
| *Slackia heliotrinireducens* DSM 20476 strain, *Gordonibacter pamelaeae* DSM 19378 strain and *Clostridium bolteae* JCM 12243 strain | Ellagic Acid 1.0 g/L | Urolithin B 0.037 g/L (molar yield, 5.3%) |

Example 5

Production of Urolithin B from Isourolithin A

Into ABB medium (manufactured by Oxoid Limited) containing 1.0 g/L isourolithin A, the *Clostridium bolteae* JCM 12243 strain, the *Clostridium asparagiforme* DSM 15981 strain or the *Clostridium citroniae* DSM 19261 strain was inoculated, and culture was performed in the same manner as in Example 1. As a result of 2 weeks of the culture, as shown in Table 6, urolithin B was obtained at molar yields 5.0%, 4.6%, and 4.1%, respectively, with respect to the isourolithin A added.

TABLE 6

| Microorganism | Substrate Isourolithin A | Product Urolithin B |
| --- | --- | --- |
| *Clostridium bolteae* JCM 12243 strain | 1.0 g/L | 0.046 g/L (molar yield, 5.0%) |
| *Clostridium asparagiforme* DSM 15981 strain | 1.0 g/L | 0.043 g/L (molar yield, 4.6%) |
| *Clostridium citroniae* DSM 19261 strain | 1.0 g/L | 0.038 g/L (molar yield, 4.1%) |

Example 6

Production of Urolithin B from Ellagic Acid

Into ABB medium (manufactured by Oxoid Limited) containing 1.0 g/L ellagic acid, the *Slackia heliotrinireducens* DSM 20476 strain and the *Gordonibacter pamelaeae* DSM 19378 strain were inoculated, and culture was performed in the same manner as in Example 1 for 15 days. To the resulting culture, the *Clostridium bolteae* JCM 12243 strain was inoculated, and the culture was further continued anaerobically at 37° C. for 4 days. As a result, as shown in Table 7, urolithin B was obtained at a molar yield of 7.3% with respect to the ellagic acid added.

TABLE 7

| Microorganism | Substrate Ellagic Acid | Product Isourolithin A | Product Urolithin B |
| --- | --- | --- | --- |
| *Slackia heliotrinireducens* DSM 20476 strain, and *Gordonibacter pamelaeae* DSM 19378 strain (Culture for 15 days) | 1.0 g/L | 0.79 g/L (molar yield, 100%) | 0 g/L (molar yield, 0%) |
| After addition of *Clostridium bolteae* JCM 12243 strain (Culture for 4 days) | — | 0.68 g/L (molar yield, 90.7%) | 0.051 g/L (molar yield, 7.3%) |

INDUSTRIAL APPLICABILITY

According to the present invention, from a urolithin having a hydroxyl group at the 8-position, another kind of urolithin in which the hydroxyl group at the 8-position is eliminated can be produced. Further, according to the present invention, urolithin B can be produced.

The urolithins and urolithin B produced may be utilized for cosmetics, quasi-drugs, medical products, sanitary articles, pharmaceuticals, foods and drinks (including supplements), and the like for the purpose(s) of antioxidation, anti-inflammation, anti-glycation, and/or the like.

All prior art documents cited in the present description are herein incorporated by reference.

The invention claimed is:

1. A method for producing a urolithin of General Formula (2), comprising:
    contacting a solution containing urolithin of General Formula (1) with a microorganism that has an ability to produce the urolithin of General Formula (2), by eliminating the hydroxyl group at position 8 of the urolithin of General Formula (1), thereby producing the urolithin of General Formula (2), wherein the microorganism belongs to the genus *Slackia*,

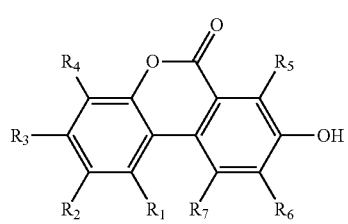

(1)

wherein $R_1$ to $R_7$ each represent a hydroxyl group, a hydrogen atom, or a methoxy group, and one or more of $R_1$ to $R_7$ represents a hydroxyl group

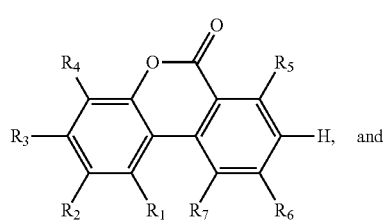

(2)

wherein $R_1$ to $R_7$ each represent a hydroxyl group, a hydrogen atom, or a methoxy group, and one or more of $R_1$ to $R_7$ represents a hydroxyl group.

2. The method of claim 1, wherein the microorganism belonging to the genus *Slackia* is a microorganism belonging to *Slackia heliotrinireducens*.

3. The method of claim 2, wherein the microorganism belonging to *Slackia heliotrinireducens* is the *Slackia heliotrinireducens* DSM 20476 strain.

4. The method of claim 1, wherein the urolithin of General Formula (1) is urolithin C, and the urolithin of General Formula (2) is isourolithin A.

5. The method of claim 4, wherein the urolithin C is obtained by contacting a solution containing a raw material of urolithin C with a microorganism having an ability to produce urolithin C from the raw material of urolithin C.

6. The method of claim 4, further comprising:
    contacting a solution containing a raw material of urolithin C with a microorganism having an ability to produce urolithin C from the raw material of urolithin C;
    wherein the steps of contacting are carried out in the same system.

7. The method of claim 1, wherein the first urolithin of General Formula (1) is urolithin A, and the urolithin of General Formula (2) is urolithin B.

8. The method of claim 7, wherein the urolithin A is obtained by contacting a solution containing a raw material of urolithin A with a microorganism having an ability to produce urolithin A from the raw material of urolithin A.

9. The method of claim 7, further comprising:
    contacting a solution containing a raw material of urolithin A with a microorganism having an ability to produce urolithin A from the raw material of urolithin A;
    wherein the steps of contacting are carried out in the same system.

10. The method of claim 1, wherein the contacting is carried out in an environment with a gas phase containing hydrogen.

11. The method of claim 10, wherein the hydrogen contains hydrogen produced using formic acid and/or a salt thereof as a raw material(s).

12. A method for producing urolithin B, the method comprising:
    contacting a solution containing a raw material of urolithin C with a first microorganism that has an ability to produce urolithin C from the raw material of urolithin C, wherein the first microorganism belongs to the genus *Gordonibacter*;
    contacting a solution containing the urolithin C with a second microorganism that has an ability to produce isourolithin A from urolithin C, wherein the second microorganism belongs to the genus *Slackia*;
    inoculating a third microorganism that has an ability to produce urolithin B from isourolithin A, into a solution containing the isourolithin A; and
    contacting the solution containing the isourolithin A with the third microorganism that has an ability to produce urolithin B from the isourolithin A, wherein the third microorganism belongs to the genus *Clostridium*; and
    wherein the method is carried out in a single system.

13. The method of claim 12, wherein the raw material of urolithin C is ellagic acid and/or ellagitannin.

* * * * *